United States Patent
Messersmith et al.

(10) Patent No.: US 9,012,594 B2
(45) Date of Patent: Apr. 21, 2015

(54) CATALYST AND BYPRODUCT-FREE NATIVE CHEMICAL LIGATION USING CYCLIC THIOESTER PRECURSORS

(75) Inventors: Phillip B. Messersmith, Clarendon Hills, IL (US); Jing Su, Chicago, IL (US); Bi-Huang Hu, Halkou (CN)

(73) Assignee: Northwestern University, Evanston, IL (US)

( * ) Notice: Subject to any disclaimer, the term of this patent is extended or adjusted under 35 U.S.C. 154(b) by 480 days.

(21) Appl. No.: 13/090,416

(22) Filed: Apr. 20, 2011

(65) Prior Publication Data

US 2011/0262492 A1  Oct. 27, 2011

Related U.S. Application Data

(60) Provisional application No. 61/326,939, filed on Apr. 22, 2010.

(51) Int. Cl.

| | |
|---|---|
| C08G 69/06 | (2006.01) |
| A61K 38/00 | (2006.01) |
| G01N 1/36 | (2006.01) |
| C07D 333/36 | (2006.01) |
| C08G 65/334 | (2006.01) |
| C08L 71/02 | (2006.01) |
| A61K 47/34 | (2006.01) |

(52) U.S. Cl.
CPC . *G01N 1/36* (2013.01); *A61K 47/34* (2013.01); *C07D 333/36* (2013.01); *C08G 65/3348* (2013.01); *C08L 71/02* (2013.01)

(58) Field of Classification Search
None
See application file for complete search history.

(56) References Cited

U.S. PATENT DOCUMENTS

| 5,610,162 | A * | 3/1997 | Witzel et al. | 514/284 |
| 6,784,174 | B1 * | 8/2004 | Cumming | 514/234.2 |
| 2008/0274980 | A1 * | 11/2008 | Messersmith et al. | 514/15 |

OTHER PUBLICATIONS

Chaterji, et al., Smart Polymeric Gels: Redefining the Limits of Biomedical Devices, Prog. Polym. Sci., 2007, 32 (8-9):1083-1122.
Dawson, et al., Synthesis of Native Proteins by Chemical Ligation, Annu. Rev. Biochem., 2000, 69:923-960.
Dirksen, et al., Strategy for the Synthesis of Multivalent Peptide-Based Nonsymmetric Dendrimers by Native Chemical Ligation, Chem. Commun., 2006, pp. 1667-1669.
Hoare, et al., Hydrogels in Drug Delivery: Progress and Challenges, Polymer, 2008, 49(8):1993-2007.
Hu, et al., Hydrogels Cross-Linked by Native Chemical Ligation, Biomacromolecules, 2009, 10(8):2194-2200.
Jung, et al., Modulating the Mechanical Properties of Self-Assembled Peptide Hydrogels Via Native Chemical Ligation, Biomaterials, 2008, 29(13):2143-2151.
Kabanov, et al., Nanogels as Pharmaceutical Carriers: Finite Networks of Infinite Capabilities, Angew. Chem. Int. Ed. Engl., 2009, 48(30):5418-5429.
Li, Materials for Immunoisolated Cell Transplantation, Advanced Drug Delivery Reviews, 1998, 33(1-2):87-109.
Miyata, et al., Biomolecule-Sensitive Hydrogels, Advanced Drug Delivery Reviews, 2002, 54:79-98.
Peppas, et al., Hydrogels in Biology and Medicine: From Molecular Principles to Bionanotechnology, Advanced Materials, 2006, 18:1345-1360.
Perale, et al., Engineering Injured Spinal Cord with Bone Marrow-Derived Stem Cells and Hydrogel-Based Matrices: A Glance at the State of the Art, Journal of Applied Biomaterials & Biomechanics, 2008, 6(1):1-8.
Richter, et al., Review on Hydrogel-Based pH Sensors and Microsensors, Sensors, 2008, 8:561-581.
Ryadnov, et al., Self-Assembled Templates for Polypeptide Synthesis, J. Am. Chem. Soc., 2007, 129 (45):14074-14081.
Slaughter, et al., Hydrogels in Regenerative Medicine, Advanced Materials, 2009, 21:3307-3329.
Su, et al., Anti-Inflammatory Peptide Functionalized Hydrogels for Insulin-Secreting Cell Encapsulation, Biomaterials, 2010, 31(2):308-314.
Suh, et al., Application of Chitosan-Based Polysaccharide Biomaterials in Cartilage Tissue Engineering: A Review, Biomaterials, 2000, 21(24):2589-2598.
Wieland, et al., Uber Peptidsynthesen. 8. Mitteilung Bildung von S-haltigen Peptiden durch intramolekulare Wanderung von Aminoacylresten, Justus Liebigs Annalen der Chemie, 1953, 583(1):129-149.
Willis, et al., A Novel Phosphorylcholine-Coated Contact Lens for Extended Wear Use, Biomaterials, 2001, 22:3261-3272.
Zimmermann, et al., Hydrogel-Based Non-Autologous Cell and Tissue Therapy, BioTechniques, 2000, 29 (3):564-581.

* cited by examiner

*Primary Examiner* — Maury Audet
(74) *Attorney, Agent, or Firm* — Quarles & Brady, LLP

(57) ABSTRACT

A method of synthesizing a biocompatible hydrogel by covalently cross-linking an effective amount of a first macromonomer including a cyclic thioester group with an effective amount of a second macromonomer including a terminal cysteine group is disclosed. In addition, the synthesis and use of the following specific cyclic thioester macromonomer that can be used in the method, as well as specific hydrogels made using this macromonomer are disclosed. The disclosed method produces a biocompatible hydrogel, while producing substantially no toxic free thiol by-product. Accordingly, the method can be used in making biomedical products, such as sutures and tissue replacement biomaterials, and for encapsulating therapeutic cells and pharmaceuticals.

22 Claims, 7 Drawing Sheets

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Gly Arg Gly Asp Ser Pro Gly
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Phe Glu Trp Thr Pro Gly Trp Tyr Gln Pro Tyr
1               5                   10
```

CATALYST AND BYPRODUCT-FREE NATIVE CHEMICAL LIGATION USING CYCLIC THIOESTER PRECURSORS

CROSS-REFERENCE TO RELATED APPLICATIONS

This application claims the benefit of U.S. Provisional Application No. 61/326,939, filed Apr. 22, 2010, the entirety of which is hereby incorporated by reference for all purposes.

STATEMENT REGARDING FEDERALLY-SPONSORED RESEARCH OR DEVELOPMENT

This invention was made with government support under Grant numbers R01 DE013030 and R01 EB003806 awarded by the National Institutes of Health. The government has certain rights in the invention.

FIELD OF THE INVENTION

This invention is directed to biocompatible macromonomers comprising a cyclic thioester moiety, a method of synthesizing such macromonomers, hydrogels and a method of forming hydrogels using such macromonomers, and methods of hydrogel functionalization using such macromonomers.

BACKGROUND OF THE INVENTION

Hydrogels are a class of highly hydrated materials with 3 dimensional networks composed of hydrophilic polymer chains, which are either synthetic or natural in origin. Because they have mechanical and structural properties similar to native tissues and the extracelluar matrix, hydrogels have been widely employed as implantable medical devices, including in contact lenses and biosensors, immunoisolating capsules for tissue transplantations, scaffolds for tissue regeneration, and materials for drug delivery. Accordingly, there is a need for biocompatible hydrogels capable of deployment by minimally invasive methods and solidification under physiological conditions.

Native chemical ligation (NCL) is the reaction between a thioester moiety and a cysteine moiety with a free a-amine group to yield an S-acyl covalent intermediate that spontaneously undergoes an S- to N-acyl migration to form a new amide bond. This mild ligation method has proven useful in chemical synthesis of large peptides and proteins and dendrimers, and has been combined with peptide self-assembly to generate polypeptides with repeated sequences. NCL has been used to increase the stiffness of hydrogels pre-assembled from β-sheet forming peptide through cross-linking of terminal thioester and cysteine groups on self-assembled linear peptides.

In our previous invention (U.S. Patent Application Publication No. 2008/0274980), we reported the successful application of native chemical ligation to cross-link soluble macromonomers to form robust, functionalized hydrogels as potential 2D and 3D-cell culture devices for organ transplantation therapy and cell-based drug delivery. However, as shown in FIG. 1, our previously disclosed method of hydrogel formation by NCL, occurring between the 4-armed cysteine terminated macromonomer 1 and 4-armed thioester-terminated macromonomer 2, releases a low molecular weight, soluble by-product (ethyl 3-mercaptopropriate, structure 3) that is potentially cytotoxic to certain cell lines.

The dose-dependent cytotoxicity of this soluble by-product has been demonstrated in, e.g., the mouse-islet derived cell line MIN6, and removal of this side product during in situ hydrogel formation is essential for improving viability of cells encapsulated in such hydrogels. Removal can be accomplished using a mini-dialysis device. However, this added toxin removal step reduces the potential of using NCL-mediated hydrogel cross-linking in biomedical applications. Due to the adverse effects of free thiol by-products, the previously disclosed method may not be usable in certain applications, such as in creating injectable materials for use in surgical sutures or for local delivery of cell and drugs.

Accordingly, a need exists for a method of preparing macromonomer-based hydrogels for biomedical applications using native chemical ligation that does not produce a toxic thiol by-product.

SUMMARY OF THE INVENTION

The present invention provides biocompatible macromonomers, hydrogels, methods of use thereof, and methods of synthesis using native chemical ligation. The invention is based on a method for bioconjugation and cross-linking of polymers to form biocompatible hydrogels. Specifically, the method encompasses a chemoselective reaction between a cyclic thioester structure and a cysteine structure. Such reaction follows the mechanism of native chemical ligation, where transthioesterification between the two reactants first gives a linked thioester-intermediate, and then this intermediate rearranges irreversibly under the usual reaction conditions to form a native amide ('peptide') bond at the ligation site (FIG. 2).

Compared to the conventional native chemical ligation reaction, the use of a cyclic thioester structure in this reaction results in formation of a single conjugate product without the release of soluble thiol-containing molecules as side products. In particular, use of this new type of native chemical ligation in cross-linking of macromonomers containing cyclic thioesters and cysteamine groups leads to formation of hydrogels in a catalyst-free and side-product-free manner. The resulting hydrogels have significantly increased biocompatibility compared to those formed from noncyclic thioester-conjugated macromonomers through the native chemical ligation mechanism. We envision such novel conjugation strategy, macromonomers containing cyclic thioesters, and methods of hydrogel formation and use using cyclic thioesters will have wide application in both basic and applied biomedical programs.

Accordingly, in a first aspect, the invention encompasses a biocompatible macromonomer having the following chemical structure:

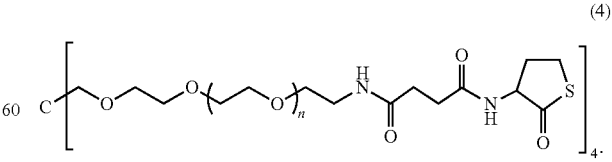

Each n in macromonomer 4 has a value in the range of from 0 to 200.

In a second aspect, the invention encompasses a hydrogel obtained by cross-linking the macromonomer having the chemical structure shown above (macromonomer 4) with a macromonomer comprising the chemical structure:

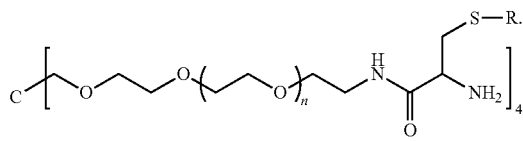

Each n has a value in the range of from 0 to 200, and each R is independently selected from H

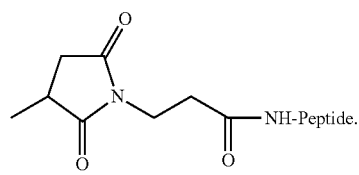

Or
In certain embodiments, R is H. In other embodiments, where at least one R is

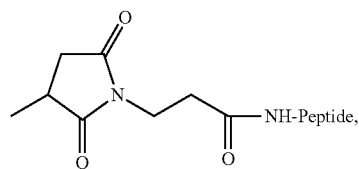

the peptide is preferably from 5 to 20 amino acid residues in length; more preferably, the peptide is from 6 to 1.2 amino acid residues in length. The peptide may include the amide-terminated amino acid sequence GRGDSPG-NH$_2$ (SEQ ID NO:1) or FEWTPGWYQPY-NH$_2$ (SEQ ID NO:2). A preferred peptide contains the sequence GRGDSPG-NH$_2$.

In certain embodiments, the hydrogel includes the chemical structure:

wherein the chemical moiety represented by

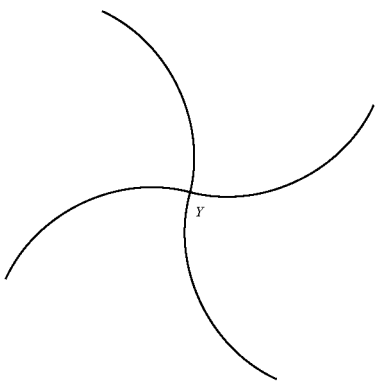

has the chemical structure:

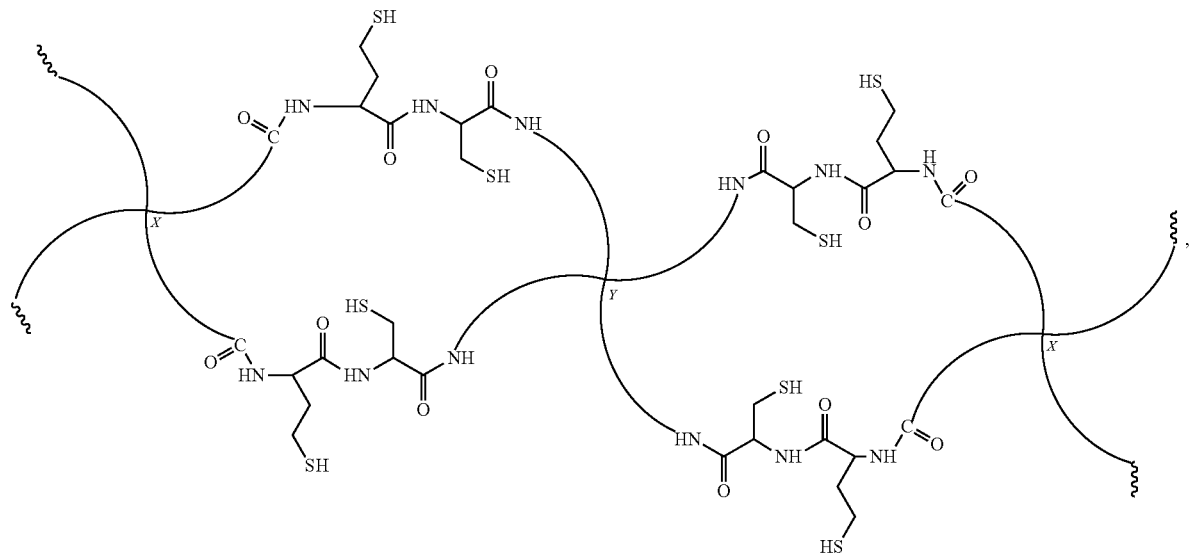

and wherein the chemical moiety represented by
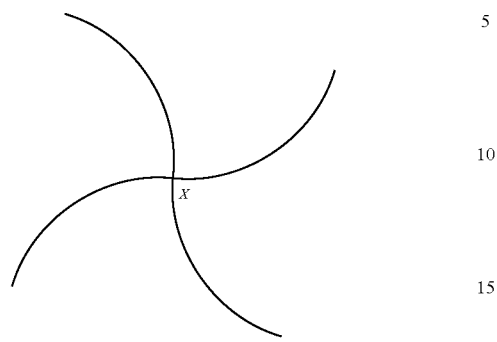
has the chemical structure:
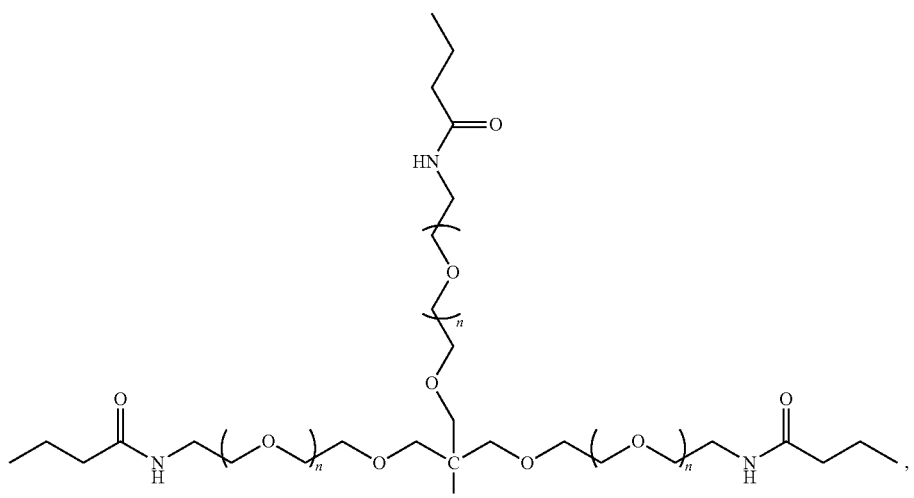
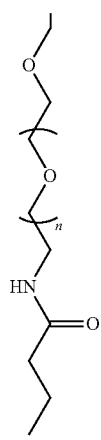
and wherein each n has a value in the range of from 1 to 201.

In other embodiments, the hydrogel includes the chemical structure:
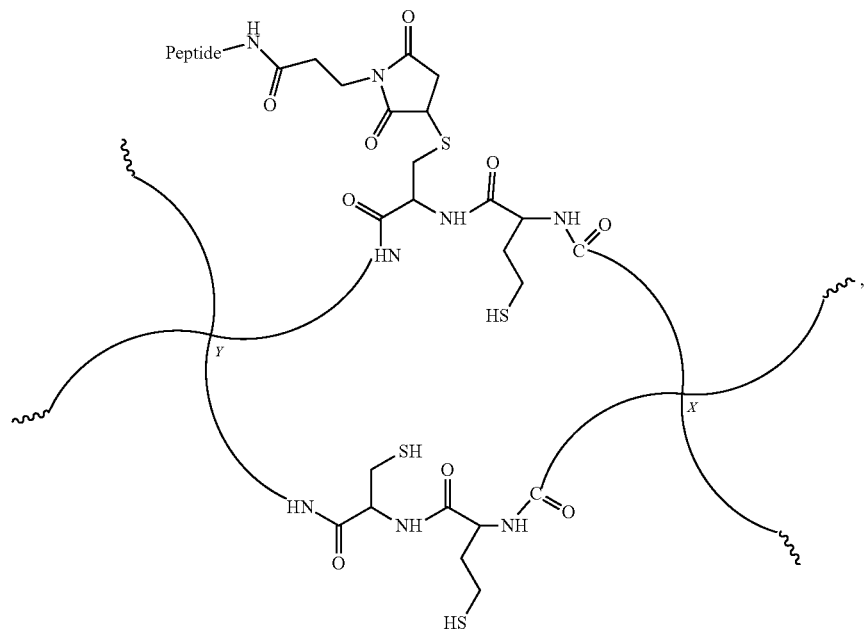
wherein the chemical moiety represented by has the chemical structure:
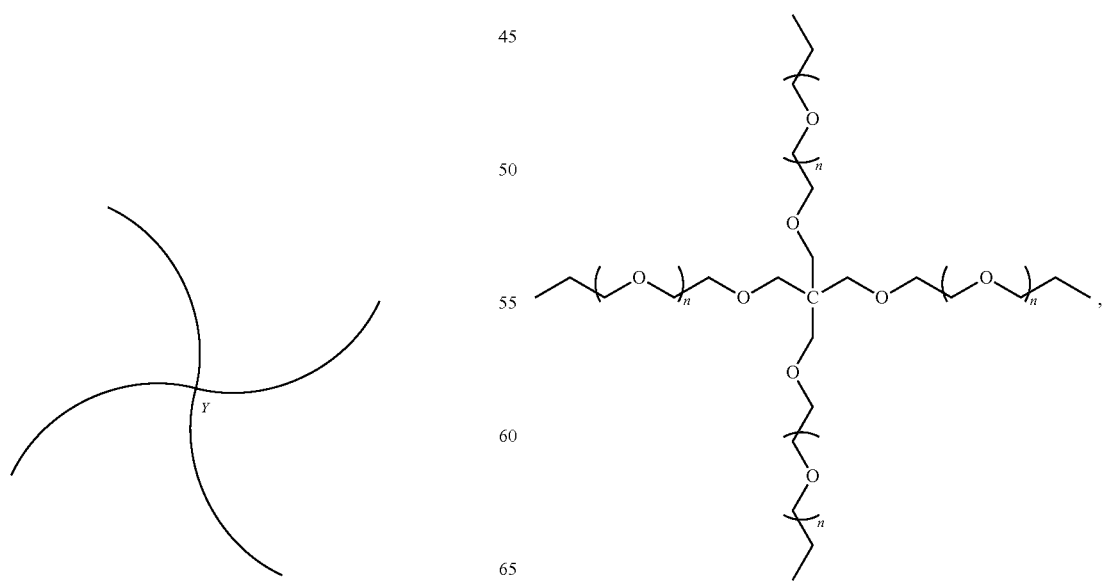

and wherein the chemical moiety represented by

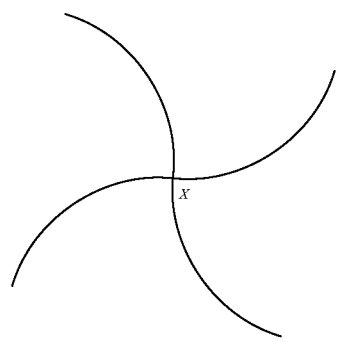

has the chemical structure:

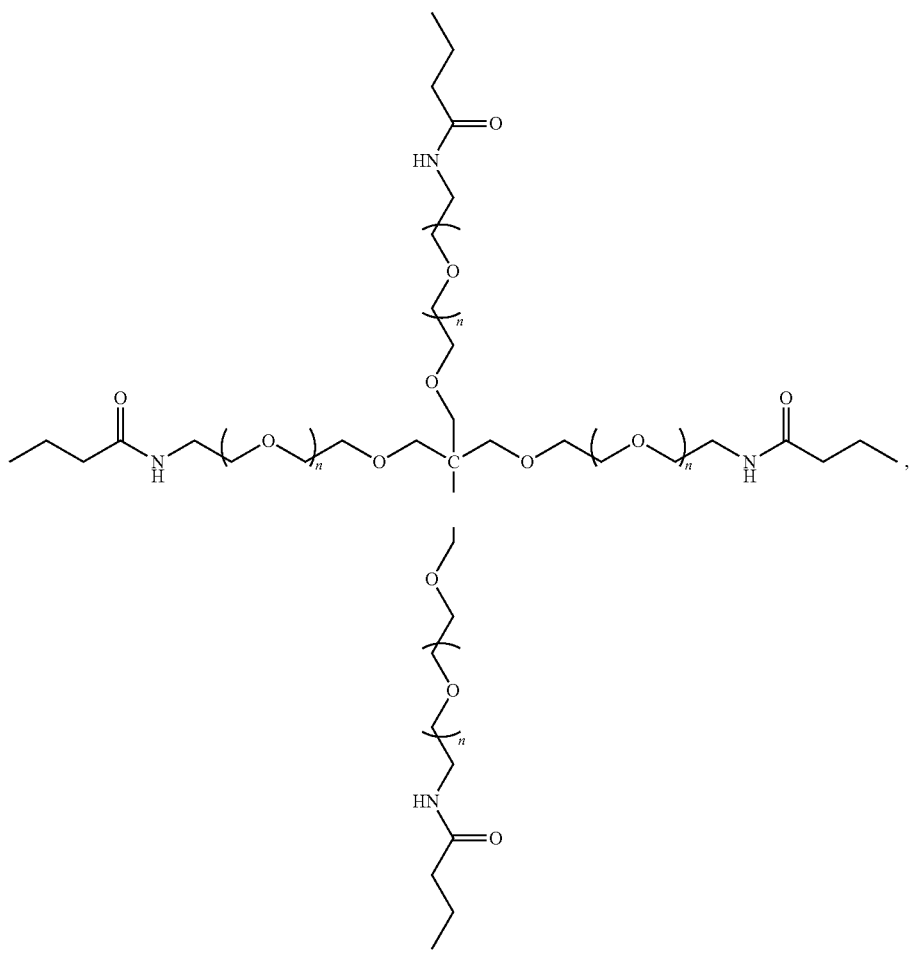

and wherein each n has a value in the range of from 1 to 20. The peptide in the structure is preferably from 5 to 20 amino acid residues in length; more preferably, the peptide is from 6 to 12 amino acid residues in length, and may include the amide-terminated amino acid sequence GRGDSPG-NH$_2$ (SEQ ID NO:1) or FEWTPGWYQPY-NH$_2$ (SEQ ID NO:2); preferably, GRGDSPG-NH$_2$ (SEQ ID NO:1).

In preferred embodiments, the hydrogels of the invention are biocompatible.

In a third aspect, the invention encompasses a method of synthesizing a hydrogel. The method includes the step of covalently cross-linking an effective amount of a first macromonomer including a cyclic thioester group with an effective amount of a second macromonomer including a terminal cysteine group, preferable using native chemical ligation, wherein a hydrogel is formed. Preferably, substantially no free thiol-containing by-product is formed in carrying out the method, and the resulting hydrogel is biocompatible.

A preferred first macromonomer for use in the method is macromonomer 4, the structure of which is shown above. Preferred second macromonomers for use in the method are also discussed above; specifically, the macromonomer having the chemical structure:

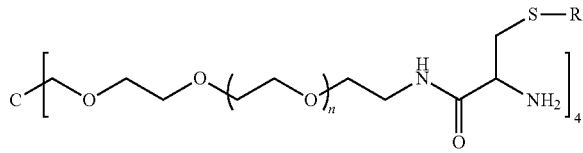

wherein each n has a value in the range of from 0 to 200, and wherein each R is independently selected from H or

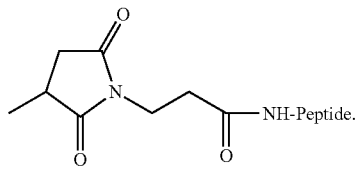

A preferred peptide is from 5 to 20 amino acid residues in length; more preferably, the peptide is from 6 to 12 amino acid residues in length. Preferred peptides include the amide-terminated amino acid sequence GRGDSPG-NH$_2$ (SEQ ID NO:1) or FEWTPGWYQPY-NH$_2$ (SEQ ID NO:2); most preferably, GRGDSPG-NH$_2$ (SEQ ID NO:1).

In a fourth aspect, the invention encompasses a method of synthesizing a macromonomer, such as the macromonomer having the chemical structure 4 shown above. The steps of the method include (a) preparing a cyclic thioester, and (b) coupling the cyclic thioester with an amine-terminated 4-armed poly(ethylene glycol).

A preferred cyclic thioester used in the method has the chemical formula:

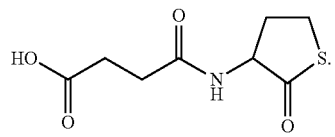

In a fifth aspect, the invention encompasses the use of the methods disclosed herein in the development of biomedical products, such as surgical sutures, tissue replacement materials and materials for the encapsulation of therapeutic cells and pharmaceuticals. In one embodiment, this aspect includes a method of encapsulating a biological sample with biomaterials. The method is carried out by a) preparing a biocompatible hydrogel according to the method of disclosed above, b) reacting the biocompatible hydrogel with a biomaterial to form a modified biocompatible hydrogel; and c) contacting the biological sample with the modified biocompatible hydrogel, wherein the hydrogel surrounds and encapsulates the sample. In certain embodiments, the biomaterial is an anti-inflammatory peptide. In such embodiments, the anti-inflammatory peptide may be an inhibitor of cell surface IL-1 receptor. Such an inhibitor may include the amino acid sequence FEWTPGWYQPY-NH$_2$ (SEQ ID NO:2).

The inventors show herein that the NCL cross-linked synthetic polymer hydrogels of the present invention are synthesized without the production of toxic free thiol side products, and that they can be functionalized with bioactive compounds. Thus, the final product is substantially free of free thiols. By "substantially free of free thiols," we mean that the concentration of free thiols in the medium in which the hydrogel is formed is insufficient to be toxic to cells which are in contact with the medium. If the cross-linking is sufficiently rapid, the hydrogel can form in-situ from a liquid precursor.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIG. 7(I) shows the amount of thiol-containing by-products released during the formation of the hydrogels shown in FIGS. 6A (A) and 6B (B). Amounts are shown in mM and were measured two hours after the commencement of hydrogel formation. Preformed gels were immersed in water to allow any molecules that were not gel-bound to diffuse into the surrounding media, and the concentration of thiol-containing species in the media was measured using Ellman's test.

DETAILED DESCRIPTION OF THE INVENTION

Figure 1:
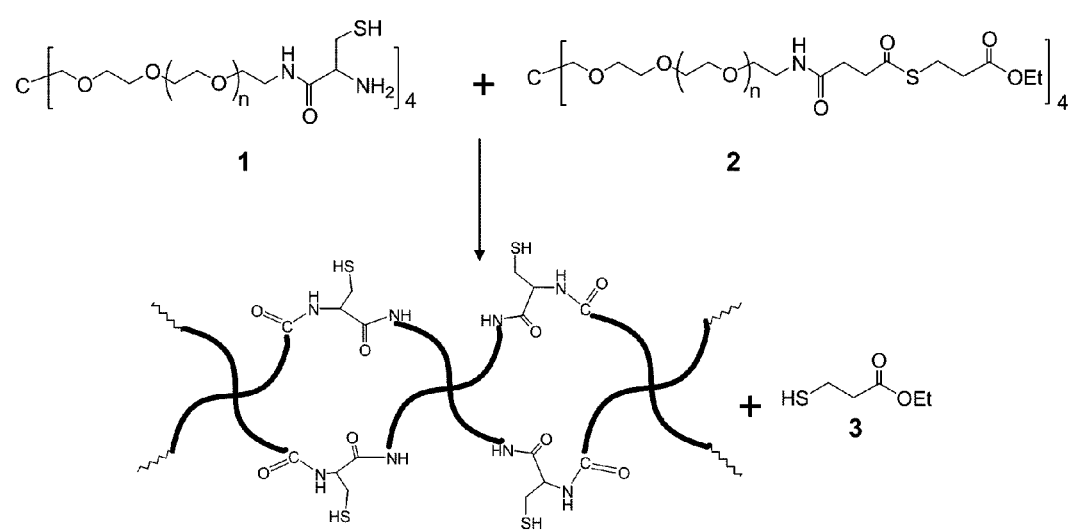
FIG. 1 is a previously disclosed reaction scheme for hydrogel formation by native chemical ligation between macromonomers 1 and 2. Note the production of the toxic soluble by-product, compound 3.

The present invention provides a new type of native chemical ligation (NCL) reaction where a cyclic thioester group is designed to react with an N-terminal cysteine group, resulting in a single product. Use of this conjugation chemistry in cross-linking macromonomers leads to formation of robust hydrogels without the release of soluble thiol side products, and therefore, such method for in situ hydrogel formation allows straightforward manipulation of materials and wide applications in tissue engineering and drug delivery. The invention provides a biocompatible macromonomer having a cyclic thioester (macromonomer 4), a method of synthesis of macromonomer 4, methods of hydrogel formation by NCL reaction with a cyclic thioester, and methods of hydrogel functionalization and uses of such hydrogels.

I. In General

In the specification and in the claims, the terms "including" and "comprising" are open-ended terms and should be interpreted to mean "including, but not limited to . . . " These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description of the hydrogels of the present invention are to be regarded as illustrative in nature and not restrictive.

II. The Invention

The present invention provides biocompatible macromonomers, biocompatible hydrogels, methods of synthesis and methods of use thereof. The biocompatible hydrogels of the present invention are prepared using native chemical ligation (NCL), in which a cyclic thioester reacts with a cysteamine (as in cysteine) through transesterification and rearrangement to form an amide bond through a five-member ring intermediate. The use of a cyclic thioester results in an NCL product that is substantially free from free thiol by-products, which may be toxic to certain cells.

A. Biocompatible Macromonomers

The present invention provides new biocompatible macromonomers comprising a cyclic thioester group. By "biocompatible" we mean a macromonomer that does not have toxic or injurious effects on biological systems and exhibits minimal local inflammatory response in surrounding tissues. For instance, the polyethylene glycol core of the preferred embodiment of the present macromonomers is well-recognized as being biocompatible, as it is non-immunogenic and resistant to nonspecific protein and cell adhesions. The macromonomers of the present invention are useful in a wide variety of applications, including, for instance, tissue repair, wound healing, drug delivery, preventing surgical adhesions, as coatings on medical devices, and thin adherent hydrogels on biosensors and chip-based diagnostic devices for genomic and proteomic assays.

In one embodiment, the invention provides a biocompatible macromonomer comprising the structure:

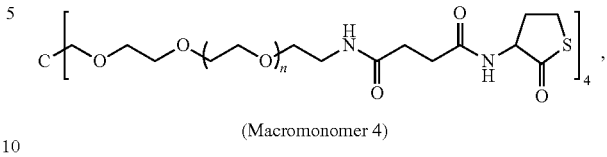

(Macromonomer 4)

wherein each n has a value in the range of from 0 to 200. Each n represents the polymeric core of the present macromonomer, and does not have to be the same value. In a preferred embodiment each n has a value ranging from 10 to 400, more preferably from 20 to 300, and further more preferably from 50 to 200. For instance, in a preferred example, the polymeric core represents 10 to 400 units of polyethylene glycol (PEG), with a total molecular weight (MW) ranging from 500 to 30,000 kDa. In other preferred embodiments the total MW of the polymeric core ranges from about 1,000 to about 20,000 kDa. While PEG comprises the polymeric core in a preferred embodiment, alternative polymeric cores including but not limited to linear or branched biocompatible polymers that can be similarly functionalized may also be used in the macromonomers of the present invention. By "functionalized" we mean modifying any linear or branched biocompatible polymer with N-terminal cysteine peptides as side chain functional groups or endgroups, or similar polymers functionalized with thioesters. In a preferred embodiment, where PEG comprises the polymeric core of the macromonomer, there are four arms emanating from the center of the macromonomer of the present invention. However, in alternative embodiments, the polymeric core could comprise six to eight or even ten to twenty different arms emanating from the center of the macromonomer.

B. Biocompatible Hydrogels

The present invention provides new biocompatible hydrogels comprising covalently cross-linked cyclic thioester-polymer and N-terminal cysteine-polymer macromonomers. In previously disclosed NCL cross-linking using straight chain thioesters, cytotoxic free thiols were released to the surrounding medium (see FIG. 1, formula 3). In contrast, in the present invention, when cross linked by NCL, the ring of the cyclic thioester is opened up to form a straight branched thiol, wherein the thiol moiety remains attached to the cross-linked polymer rather than being released to the surrounding medium.

By "biocompatible" we mean a hydrogel that does not have toxic or injurious effects on biological systems. The hydrogels of the present invention are useful in a wide variety of applications, including, for instance, medically useful devices or implants that can release bioactive compounds in a controlled manner for local, systemic, or targeted drug delivery; medically useful devices or implants for use as surgical adhesion prevention barriers, implantable wound dressings, scaffolds for cellular growth for tissue engineering or as surgical tissue adhesives or sealants; biomaterials for preventing transplant rejection; and other medically useful applications such as hydrogel coatings for preventing bacterial infection of medical device surfaces, and coatings for chip-based assays of DNA, RNA or proteins.

In one embodiment, the invention comprises a biocompatible hydrogel according to the structure:
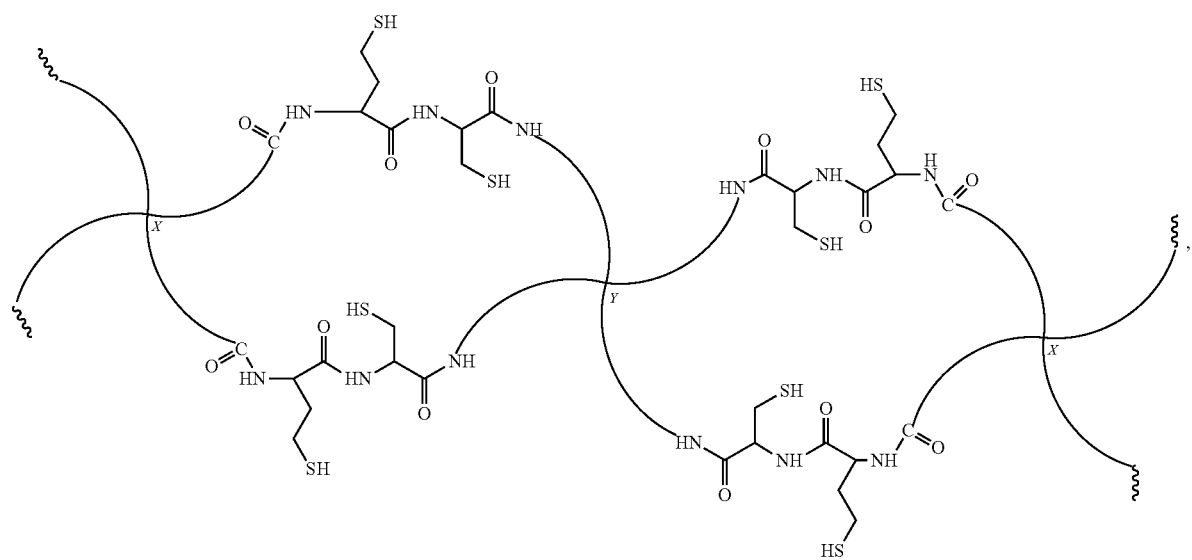
wherein the chemical moiety represented by
has the chemical structure:
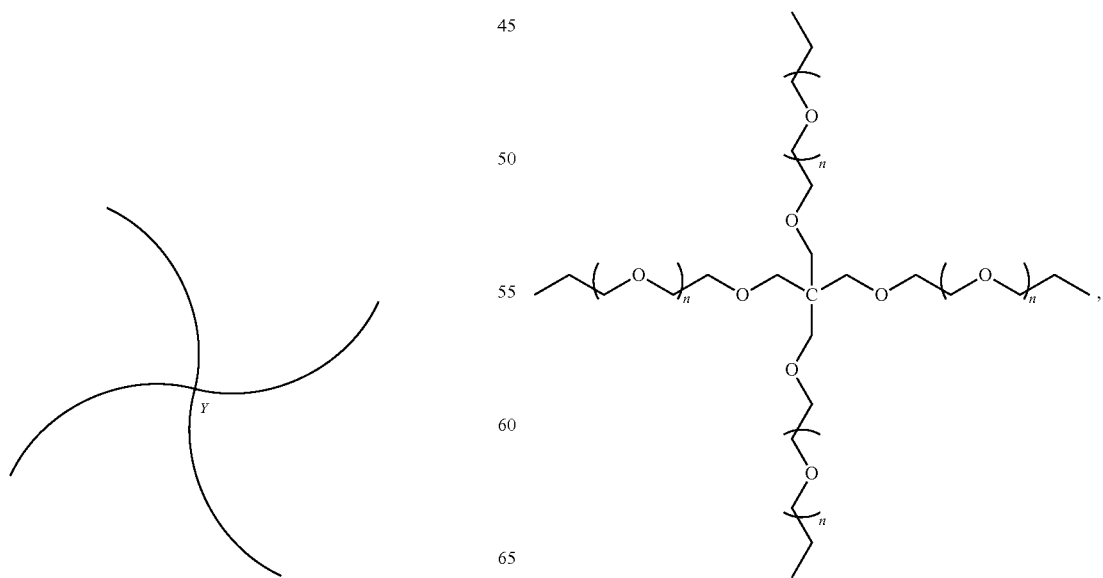

and wherein the chemical moiety represented by

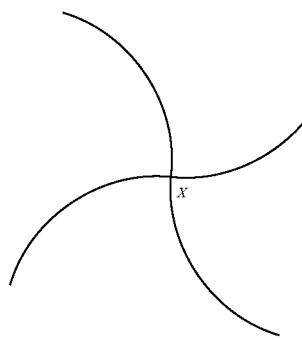

has the chemical structure:

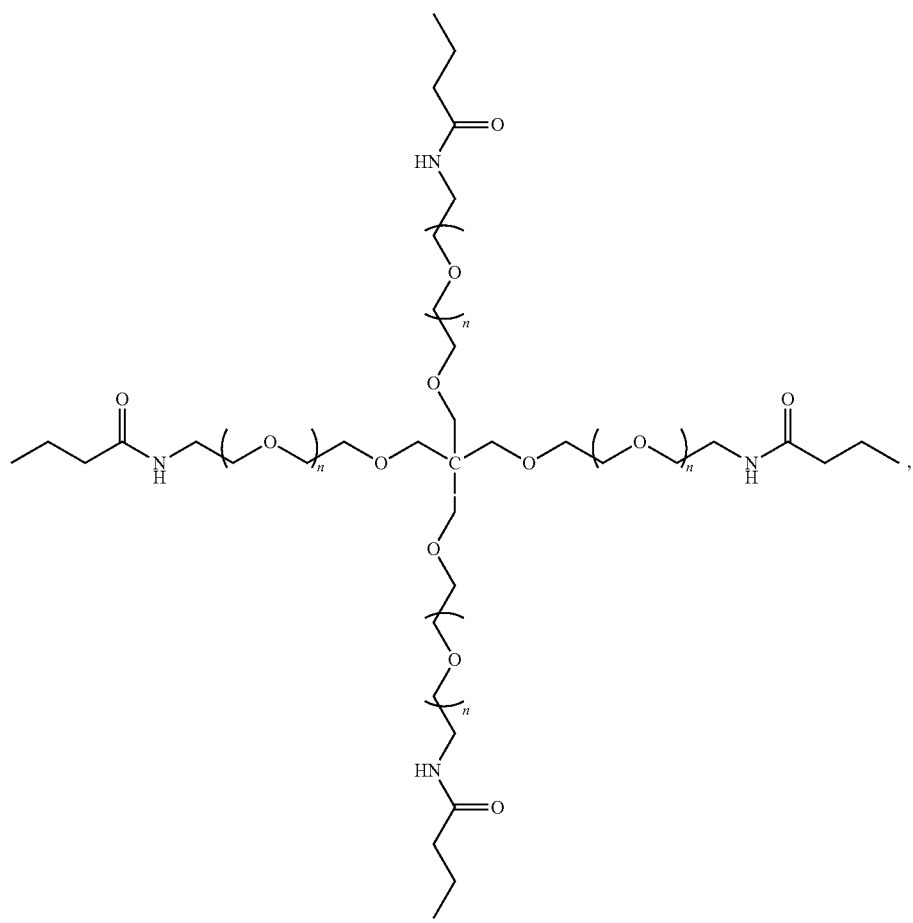

and wherein each n has a value in the range of from 1 to 201.

This hydrogel is formed by covalently cross-linking through NCL the macromonomer 4 and the macromonomer having the chemical structure:

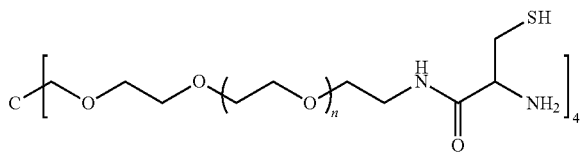

(Macromonomer 1). Each n represents the polymeric core of the present macromonomer, and does not have to be the same value. In a preferred embodiment each n has a value ranging from 10 to 400, more preferably from 20 to 300, and further more preferably from 50 to 200. For instance, in a preferred example, the polymeric core represents 10 to 400 units of polyethylene glycol (PEG), with a total molecular weight (MW) ranging from 500 to 30,000 kDa. In other preferred embodiments the total MW of the polymeric core ranges from about 1,000 to about 20,000 kDa. While PEG comprises the polymeric core in a preferred embodiment, alternative polymeric cores including but not limited to linear or branched biocompatible polymers that can be similarly functionalized may also be used in the macromonomer of the present invention. By "functionalized" we mean modifying any linear or branched biocompatible polymer with N-terminal cysteine peptides as side chain functional groups or endgroups, or similar polymers functionalized with thioesters. In a preferred embodiment, where PEG comprises the polymeric core of the macromonomer, there are four arms ("n") emanating from the center of the macromonomer of the present invention. However, in alternative embodiments, the polymeric core could comprise six to eight or even ten to twenty different arms emanating from the center of the macromonomer. Equivalent amounts of the macromonomers are preferred, although other ratios of macromonomers are envisioned, including but not limited to ratios ranging from 0.25:1, 0.5:1, 0.75:1, 1:1, 1.25:1, 1.5:1, 2:1, etc.

In alternate embodiments, the invention comprises a biocompatible hydrogel formed by covalently cross-linking the macromonomer 4 to a functionalized variant of the second macromonomer 1, wherein each n has a value ranging from 0 to 200. Equivalent amounts of the macromonomers are preferred, although other ratios of macromonomers are envisioned, including but not limited to ratios ranging from 0.25:1, 0.5:1, 0.75:1, 1:1, 1.25:1, 1.5:1, 2:1, etc.

C. Methods of Synthesis

Figure 2:
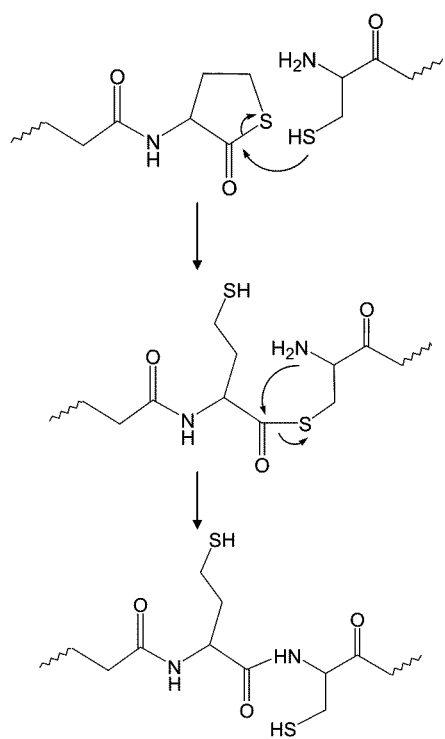
FIG. 2 is a reaction mechanism for a native chemical ligation reaction between a molecule containing a cyclic thioester (homocysteine thiolactone) and a molecule having a terminal cysteine moiety with a free a-amine group.
Figure 4:
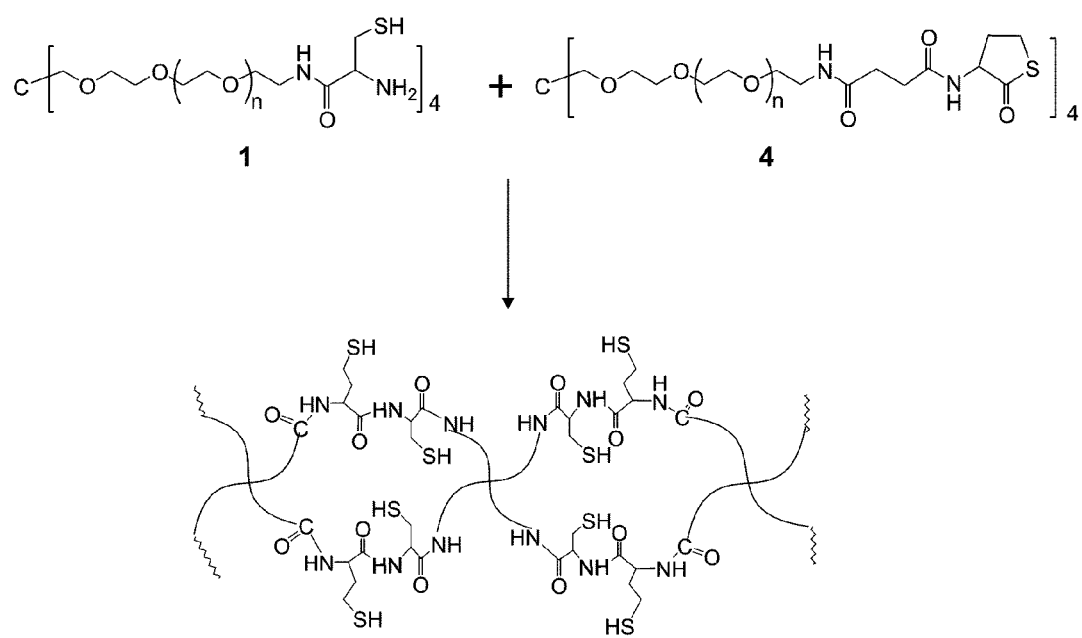
FIG. 4 is a reaction scheme illustrating the synthesis by native chemical ligation of a hydrogel by cross-linking a macromonomer containing a terminal cyclic thioester group with a macromonomer having a terminal cysteine moiety with a free α-amine group. No toxic byproduct is formed.
Figure 5:
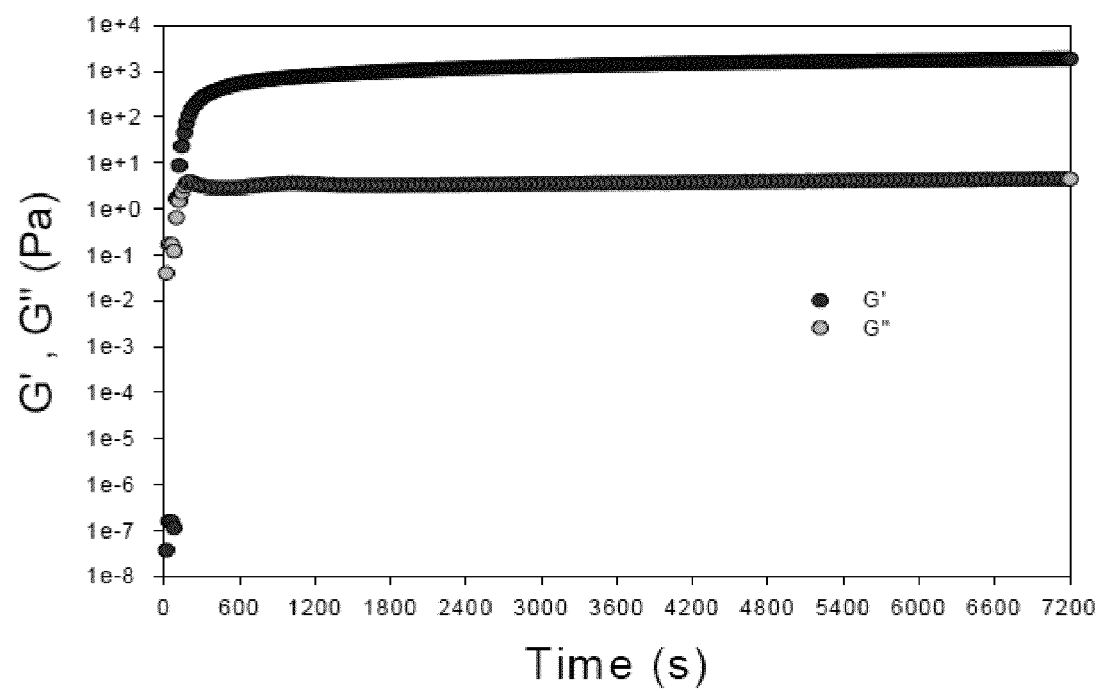
FIG. 5 shows oscillatory rheology of the native chemical ligation hydrogel formation shown in FIG. 4. Time test was performed at a constant oscillation frequency of 1 Hz and constant strain of 1%, at a controlled temperature (20° C.) by mixing 1 of FIG. 4 (5%, w/v) and 4 of FIG. 4 (5%, w/v). G' is storage modulus and G" is loss modulus.

The invention also provides novel methods of synthesis of the biocompatible macromonomers and hydrogels described above. In general, the inventors first synthesized a first polymer macromonomer containing a cyclic thioester (FIG. 3) and a second polymer macromonomer containing an N-terminal cysteine residue. The macromonomers were then covalently cross-linked using NCL (FIG. 2) to form biocompatible hydrogels (FIG. 4). The reaction conditions described herein lead to rapid hydrogel formation by NCL, and the viscoelastic behavior of the hydrogels was measured by oscillatory rheology (FIG. 5).

The methods comprise cross-linking a 4-armed PEG cysteine (4A-PEG-Cys; macromonomer 1) and a 4-armed PEG cyclic thioester (4A-PEG-CThE; macromonomer 4) through NCL to form a biocompatible hydrogel. The advantages of using NCL methods as compared to other synthetic hydrogel formation techniques are that the reaction is very specific and biocompatible. The covalent cross-linking is mostly limited between the cystine and cyclic thioester groups on the PEG molecules, whereas in other hydrogel forming methods cross-linking can also occur between the synthetic macromonomers and biological components such as cell surface proteins and agents in the culture media. The hydrogel formation occurs under mild physiological conditions (pH 7-9), bearing a minimal toxicity to the cells during encapsulation. Furthermore, the resultant hydrogel presents thiol groups that promote cell adhesion inside the hydrogel network and their mild reductive properties can also be used to protect encapsulated cells from oxidative stress.

The advantage of using a cyclic thioester macromonomer as compared to other thioester macromolecules is that free thiols, which have significant cytotoxicity, are not produced in the reaction and released to the surrounding medium. Instead, the ring opens up and a thiol group is retained on a side chain of the macromonomer. Thus, the cells in contact with the hydrogel are not affected by the presence of free thiols, and there is no need to remove free thiols from the medium in order to protect cell viability as the hydrogel is formed.

The methods of macromonomer and hydrogel formation described herein provide biocompatible macromonomers and hydrogels which are easily modified with bioactive materials to improve functions of encapsulated cells such as supporting cell growth, and the development and secretion of cellular products upon biological stimulus. By "bioactive" we mean a substance that has or cause an effect on in biological samples. In this work, the macromonomers and hydrogels were further functionalized with peptides, although other bioactive materials may be used, such as proteins, growth factors, DNA, RNA. Peptides were functionalized through the Michael addition reaction between 4A-PEG-Cys and maleimide-terminated peptides prior to the cross-linking between 4A-PEG-Cys and 4A-PEG-CThE. This reaction is quantitative and fast, providing a good control over the density of peptides attached to the resulted hydrogel. Such strategy works well, when the physiological effects of peptides on cells can be achieved at low immobilization density. For example, presence of the cell adhesion peptide GRGDSPG at 1% of the total cysteine groups used for hydrogel formation was sufficient to support cell adhesion in our case.

However, other methods of functionalization are also incorporated in the scope of this invention. For instance, other methods of functionalization may be used if more peptides need to be presented (e.g., above 10% of total cysteine groups on 4A-PEG-Cys). One of these methods is to use peptide-incorporated Cys-PEG macromonomers (bioactive peptide conjugated between Cys and PEG moiety on one or multiple arms of PEG4) to form the hydrogel by NCL and present peptides on high densities. Cross-linking polymers through NCL allows the use of multiple strategies known to the art for hydrogel functionalization according to the present invention.

In one embodiment, the invention provides a method of synthesizing a biocompatible macromonomer comprising the structure:

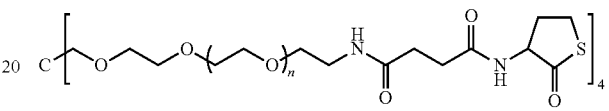

(Formula 4), wherein each n has a value in the range of from 0 to 200, the method comprising preparing a cyclic thioester and coupling the cyclic thioester with an amine-terminated 4-armed poly(ethylene glycol). In a preferred embodiment the cyclic thioester is:

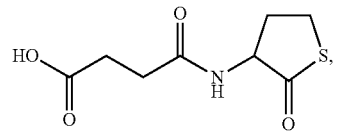 [SMILES: O=C(O)CCC(=O)NC1CCSC1=O]

although other cyclic thioesters are encompassed in the scope of this invention. In a preferred embodiment the amine-terminated 4-armed poly(ethylene glycol) is PEG4, although other poly(ethylene glycols) may also be used.

D. Methods of Use

The biocompatible macromonomers and hydrogels of the present invention are useful in a wide variety of medically useful devices and implants. For instance, the biocompatible macromonomers of the present invention are useful in applications ranging from tissue repair, wound healing, drug delivery, preventing surgical adhesions, as coatings on medical devices, and thin adherent hydrogels on biosensors and chip-based diagnostic devices for genomic and proteomic assays.

The biocompatible hydrogels of the present invention are useful in forming medically useful devices or implants that can release bioactive compounds in a controlled manner for local, systemic, or targeted drug delivery. Further, the biocompatible hydrogels are useful in forming medically useful devices or implants for use as surgical adhesion prevention barriers, implantable wound dressings, scaffolds for cellular growth for tissue engineering or as surgical tissue adhesives or sealants. Further still, the biocompatible hydrogels are useful in forming peptide-functionalized hydrogels which can protect transplanted tissue from rejection, specifically, the peptide-functionalized hydrogels can protect pancreatic islet cells from inflammatory response post-transplantation.

In one embodiment, the present invention provides a method of encapsulating a biological sample with biomaterials comprising preparing a biocompatible hydrogel according to the methods described above, reacting the biocompatible hydrogel with a biomaterial to form a modified biocompatible hydrogel and contacting the biological sample with the modified biocompatible hydrogel, wherein the hydrogel surrounds and encapsulates the sample. By "biological sample" we mean to include a specimen or culture obtained from any source. Biological samples can be obtained from animals (including humans) and encompass fluids, solids, tissues, and gases. Biological samples include blood products, such as plasma, serum and the like. Such examples are not however to be construed as limiting the sample types applicable to the present invention.

By "biomaterials" we mean materials selected from the group consisting of anti-inflammatory agents, cell function promoting agents, various artificial implants, pacemakers, valves, catheters, and membranes (e.g., a dialyzer), as well as synthetic polymers such as polypropylene oxide (PPO) and polyethylene glycol (PEG). In a further preferred embodiment the biomaterial is an anti-inflammatory peptide such as an inhibitor of cell surface IL-1 receptor.

In certain embodiments, a 4-armed PEG-cysteine is reacted with at least one peptide before being cross-linked with a 4-armed PEG cyclic thioester. In preferred embodiments, the peptide is a maleimide-terminated peptide selected from the group consisting of collagen, fibrinogen, albumin, and fibrin, polysaccharides and glycosaminoglycans, although other types of peptides may also be used. For instance, in certain such embodiments, the peptides are GRGDSPG (SEQ ID NO:1) or FEWTPGWYQPY (SEQ ID NO:2) wherein both peptides are modified at the terminus end with an amine group $-NH_2$, i.e., GRGDSPG-$NH_2$ and FEWTPGWYQPY-$NH_2$.

D. Kits

In an alternate embodiment of the invention, a kit for preparing the biocompatible macromonomers and hydrogels of the present invention is provided. In one embodiment, the kit comprises a biocompatible macromonomer having a cyclic thioester group, such as macromonomer 4, and instructions for use. The kit may also include other biocompatible macromonomers, such as the 4A-PEG-Cys (macromonomer 1) or functionalized 4A-PEG-Cys as described above.

In a preferred embodiment, the kit comprises a powdered form of at least one of the biocompatible macromonomers, wherein the powdered macromonomer is hydrated by the user for immediate use, such as in a dual syringe device to form a precursor liquid that rapidly gels. Optionally, the kit may contain a solution for dissolving the macromonomer.

In another preferred embodiment, the kit comprises at least one of the biocompatible hydrogels discussed above and instructions for use.

In an alternate embodiment, the kit comprises a biocompatible hydrogel according to the present invention formulated, delivered and stored for use in physiologic conditions.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention. Alternatively, the instructional material can be shipped separately from the container or provided on an electronically accessible form on a internet website with the intention that the instructional material and the biocompatible hydrogel be used cooperatively by the recipient.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. EXAMPLES

Example 1

Methods of Macromonomer Synthesis

A. Synthesis of Cyclic Thiester Used to Make Macromonomer Formula 4

Figure 3:
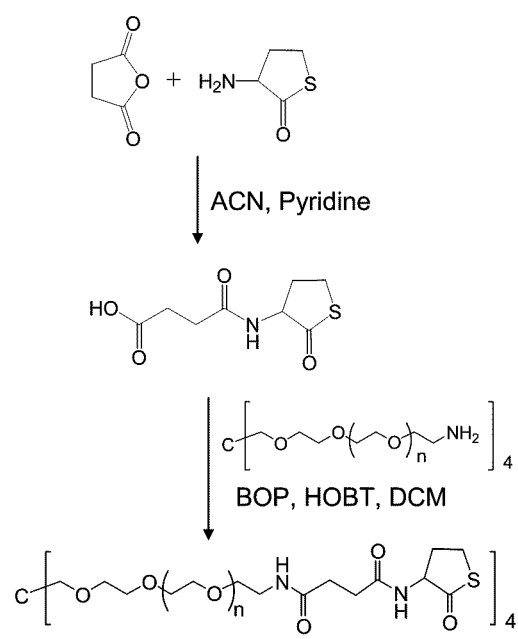
FIG. 3 is a reaction scheme illustrating the synthesis of a specific macromonomer containing a terminal cyclic thioester group.

As shown in FIG. 3, the compound

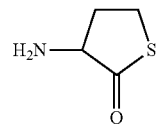

was added under argon to a stirring solution of succinic anhydride in 25 ml of acetonitrile-pyridine (9:1). The reaction mixture was stirred at room temperature overnight. The solution was concentrated under reduced pressure and dried in vacuo. The residue was dissolved in 50 ml of EtOAc. The EtOAc solution was washed with 0.1 N HCl aqueous solution 30 ml×3, $H_2O$×3, dried over anhydrous $MgSO_4$. After filtration, the solution was concentrated to dry under reduced pressure and in vacuo. NMR spectroscopy data confirmed the product formula:

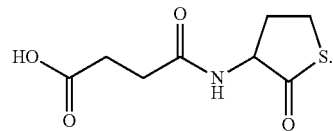

B. Materials for Macromonomer Synthesis.

4-armed PEG with amine end groups ($\overline{M}_w$=10k) (PEG4A) was purchased from SunBio PEG Shop. BOP and HOBT were purchased from Peptide International (Louisville, Ky.).

C. Synthesis of Macromonomer-Formula 4

As further illustrated in FIG. 3, a solution of the product of (A) above in DCM was added into a vial containing PEG4A and BOP, followed by addition of HOBT. The mixture was vortexed for 5 min, and rocked for 2 hrs. The reaction was monitored by silica gel TLC (solvent system DCM-MeOH-HOAc=100:3:1). The spots on the TLC plate were visualized by spray of 1% ninhydrin solution in ethanol containing 3% HOAc and heat at 105° C. The purification of the product was performed by dilution with MeOH to a final volume of 50 ml. The solution was shaken well and frozen at −20° C. The precipitate was collected by centrifugation (−9° C., 6000 rpm, 20 min) and decanting the solvent. The purification cycle of four steps of dissolution in MeOH at room temperature, freeze at −20° C., centrifugation at −9° C. and decanting the MeOH was repeated for four times, and followed by precipi tation with diethyl ether and dried in vacuo. NMR spectroscopy data confirmed the product formula:

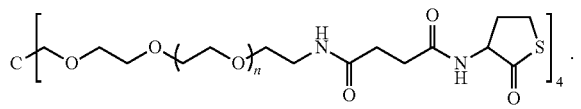

D. Synthesis of Peptides and Functionalizing Macromonomers Used to Make Hydrogels The maleimide-terminated peptide MA-GRGDSPG-NH$_2$ (SEQ ID NO:1) was synthesized using standard solid phase peptide synthesis protocols on Rink amide resin (0.69 meq/g) at 0.1 mmol scale. Each coupling step was carried out by mixing 3 equivalents of Fmoc protected amino acids, PyBop and NMM with the resin beads for 4 hours on a rocker. After the resin beads were washed thoroughly with DMF, 20% piperidine in DMF was used to deprotect Fmoc group to expose the amine groups on the beads for next coupling step. After the last amino acid was conjugated, maleimide-OSU ester (2 eqv.) in DMF was used to attach the maleimide moieties to the N-terminal of resin-bound peptides. Cleavage of the maleimide-terminated peptides from the resin and deprotection of the amino acid side chains was accomplished by treating the resin with 95% (v/v) TFA, 2.5% H$_2$O and 2.5% TIS for 2 hours at room temperature, after which the cleaved peptides were collected by filtering and rinsing resins several times with TFA. Solvent was removed using a rotary evaporator; the product residues were dissolved in a minimal amount of TFA and precipitated with cold ether and by centrifugation at 4° C. The product pellets were dissolved in deionized water, frozen and lyophilized. Crude products were purified by preparative RP-HPLC.

Figure 6:
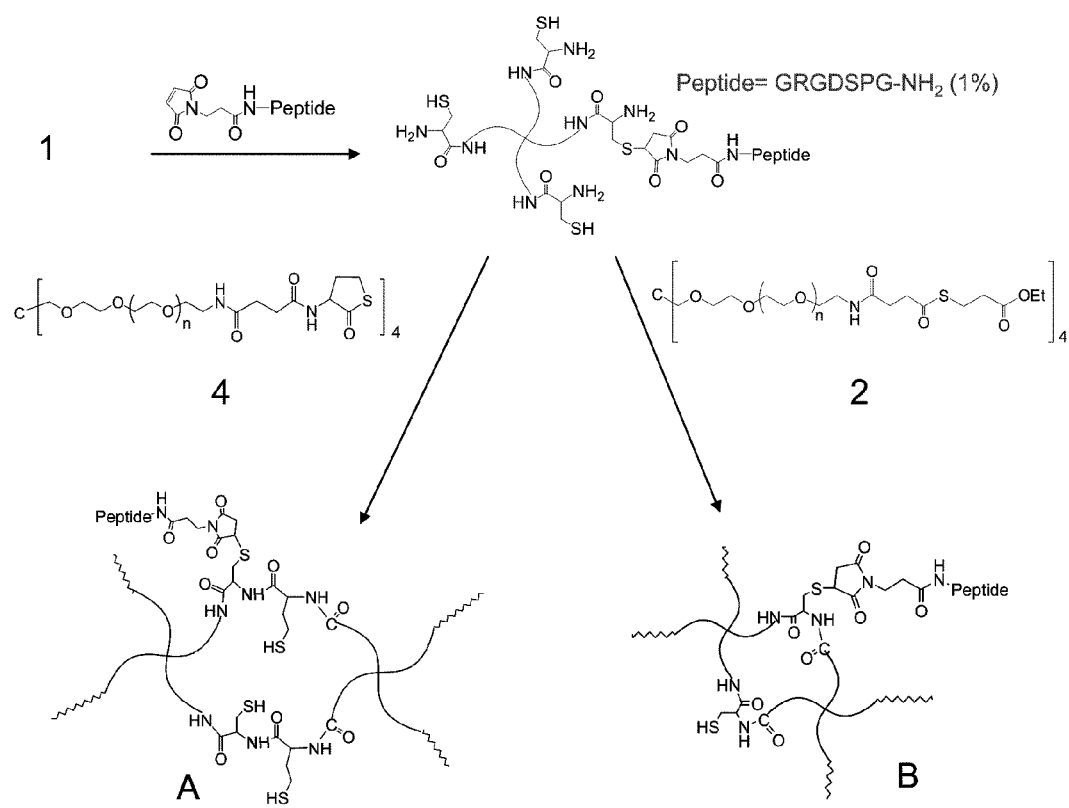
FIG. 6 is a reaction scheme showing the formation of peptide-functionalized hydrogels A and B by native chemical ligation using macromonomers 1 and 2 (FIG. 6A) or 1 and 4 (FIG. 6B). The peptide is GRGDSPG-NH$_2$ (SEQ ID NO:1).

The resulting maleimide-terminated peptide MA-GRGD-SPG-NH$_2$ was linked to 4A-PEG-Cys (Formula 1 in FIGS. 1 and 4) via Michael addition (see FIG. 6, top line).

Example 2

Synthesis of Biocompatible Hydrogels

A. Gel Formation.

In this example, the inventors evaluated gel formation of the hydrogels by mixing cyclic thioester-polymer bioconjugate 4 in pure water (solution A) and N-terminal cysteine-polymer bioconjugate 1 in a buffer solution (solution B) (See FIG. 4). Hydrogels were formed by adding solution B into a test tube (100×13 mm) containing solution A and a moving stirring bar (10×3 mm). Unless otherwise indicated, the mixtures were equimolar in cyclic thioester-polymer and N-terminal cysteine-polymer. Using a stopwatch, the gel formation time was recorded when movement of the stir bar stopped as a result of gel formation.

B. Viscoelastic Behavior of Hydrogels

To characterize the viscoelastic behavior of the hydrogels formed by NCL using a cyclic thioester, the hydrogel system produced as described above and in FIG. 4 was analyzed further by oscillatory rheology. Oscillatory rheological experiments were performed with a Paar Physica MCR300 Rheometer with a Peltier device to control temperature at 20° C. using a stainless steel cone/plate fixture (50 mm in diameter, 1° cone). In a typical experiment, the bioconjugate solutions were prepared as follows: Solution A 5% of 4 in water and Solution B 5% of 1 in water, pH 8.3. 500 µl each of solution A and solution B were added into a vial. After vor-texing, 590 µl of the solution was immediately loaded onto the thermostated rheometer plate (20° C.), and the top cone (50 mm in diameter, 1° cone) was positioned to hold the solution in a 0.05 mm gap at the center between the cone and plate. After moisturized Kimwipes paper was applied to surround the cone/plate fixture for evaporation control, data were collected every 20 s over a 120 minute span. The time dependence of the viscoelastic behavior was measured at a constant oscillation frequency of 1 Hz and constant strain of 1%, at a controlled temperature (20° C.). The time dependent changes in storage modulus (G') and loss modulus (G") for all NCL hydrogels tested were characteristic of elastic hydrogel formation (FIG. 6) as indicated by a low initial G', a G'/G" crossover point representing a theoretical gel condition, followed by rapid increase in G' to a plateau value as the NCL reaction becomes complete.

Note that the characteristic crossover point was reached well before the ten minute (600 seconds) mark. The stiffness of the fully cured NCL hydrogels was remarkably high as illustrated by a plateau modulus value. The measurements of the storage modulus and loss modulus were taken at 20° C. in the oscillatory mode at 1 Hz frequency and 1% strain during cross-linking.

D. Reduced Free Thiols Release From Hydrogels Made From Cyclic Thioester Macromonomers In a comparative study, the hydrogels formed by native chemical ligation between macromonomers 1 and 2 (using a straight chain thioester) and macromonomers 1 and 4 (using a cyclic thioester) were separately carried out under identical conditions (buffer, pH, temperature, time and concentrations of reagents). The formation of the two different hydrogels is illustrated in FIG. 6, where the hydrogel formed from the cyclic thioester macromonomer 4 is labeled hydrogel A, and the hydrogel formed from the straight chain thioester macromonomer 2 is labeled hydrogel B. Note that both hydrogels used NCL cross-linking to a macromonomer 1 that is further functionalized by the maleimide-terminated peptide MA-GRGDSPG-NH$_2$, as discussed in the previous Example (see FIG. 6).

Figure 7:
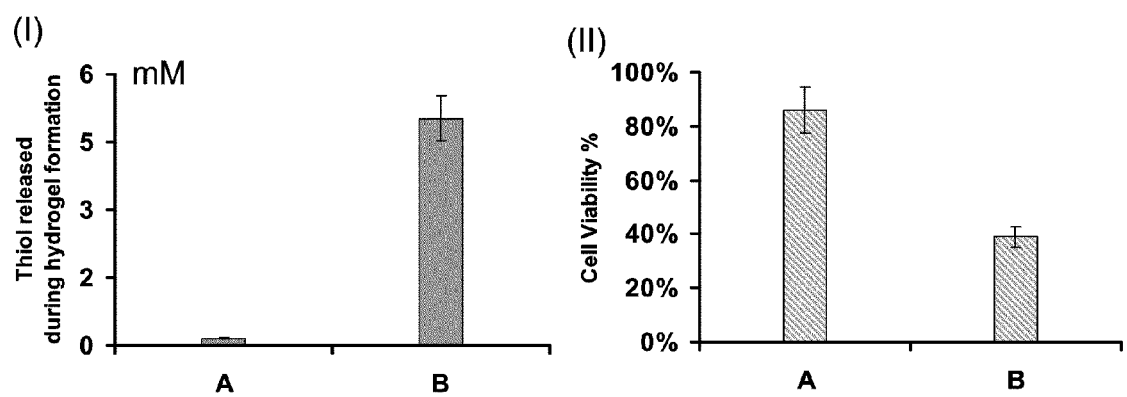
FIG. 7(II) shows cell viability data for the hydrogels shown in FIGS. 6A (A) and 6B (B). MIN6 cells were directly seeded onto gels after the gels were allowed to form for two hours at 37° C. Viability was measured 24 hours later using a fluorescent cell viability assay (calcein-AM for live and ethidium homodimer-1 for dead cells).

The preformed gels were immersed in water to allow any molecules that are not gel-bound to diffuse out of gels into surrounding media. The concentration of thiol-containing species in the media was measured using Ellman's test, as shown in FIG. 7 (I). Hydrogel A, formed between 1 and 4 (the cyclic thioester) produced minimal amount of soluble thiol-containing species. In contrast, hydrogel B, formed between 1 and 2, produced high concentration of soluble thiol side product, consistent with our previous studies (see FIG. 1).

E. Increased Cell Viability on Hydrogels Made From Cyclic Thioester Macromonomers The mouse insulinoma cell line (MIN6) used for this study was a gift from Dr. Dixon Kaufman's lab in the Department of Surgery at Northwestern University. Cells were cultured in the DMEM medium containing 15% FBS, penicillin, streptomycin and 50 µM MCE at 37° C. under 5% CO$_2$. Cells between passage number 25 and 28 were used for this study.

Hydrogel A and Hydrogel B (FIG. 6) were formed for two hours at 37° C., as previously described. MIN6 cells that were detached from tissue culture plates with a 0.25% trypsin-EDTA solution and resuspended in DMEM at a cell density of 4×10$^5$/mL were directly cultured on these preformed gels, without rinsing, for 24 hours.

After 24 hours, a cell viability assay was performed. The MIN6 cells cultured on the preformed hydrogels were incubated with a PBS solution containing calcein-AM (1 µM) and ethidium homodimer-1 (1 µM) for 30 minutes at 37° C. The cells were imaged on an inverted fluorescence microscope.

Cell viability was determined as the ratio of the number of live cells divided by the total number of live and dead cells (FIG. 7(II)). The cells showed greatly improved viability on hydrogel A compared to hydrogel B, showing a correlation between loss of cell viability and the production of soluble, cytotoxic free thiol side products released during the formation of hydrogel B. In contrast, when forming hydrogel A using the cyclic thioester 4, no such free side products are made (FIG. 7(I)), leading to increased cell viability.

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

This application is submitted with a sequence listing in computer readable form. The sequences in the listing are the same as those referenced throughout the application for SEQ ID NO:1 and SEQ ID NO:2, and the sequence listing is incorporated by reference herein.

REFERENCES (1) Peppas, N. A.; Hilt, J. Z.; Khademhosseini, A.; Langer,. R. *Advanced Materials* 2006, 18, 1345.

(2) Willis, S. L.; Court, J. L.; Redman, R. P.; Wang, J. H.; Leppard, S. W.; O'Byrne, V. J.; Small, S. A.; Lewis, A. L.; Jones, S. A.; Stratford, P. W. *Biomaterials* 2001, 22, 3261.

(3) Miyata, T.; Uragami, T.; Nakamae, K. *Advanced Drug Delivery Reviews* 2002, 54, 79.

(4) Chaterji, S.; Kwon, I. K.; Park, K. *Progress in Polymer Science* 2007, 32, 1083.

(5) Richter, A.; Paschew, G.; Klatt, S.; Lienig, J.; Arndt, K. F.; Adler, H. J. P. *Sensors* 2008, 8, 561.

(6) Li, R. H. *Advanced Drug Delivery Reviews* 1998, 33, 87.

(7) Zimmermann, U.; Mimietz, S.; Zimmermann, H.; Hillgartner, M.; Schneider, H.; Ludwig, J.; Hasse, C.; Haase, A.; Rothmund, M.; Fuhr, G. *Biotechniques* 2000, 29, 564.

(8) Suh, J. K. F.; Matthew, H. W. T. *Biomaterials* 2000, 21, 2589.

(9) Slaughter, B. V.; Khurshid, S. S.; Fisher, O. Z.; Khademhosseini, A.; Peppas, N. A. *Advanced Materials* 2009, 21, 3307.

(10) Perale, G.; Bianco, F.; Giordano, C.; Matteoli, M.; Masi, M.; Cigada, A. *Journal of Applied Biomaterials & Biomechanics* 2008, 6, 1.

(11) Hoare, T. R.; Kohane, D. S. *Polymer* 2008, 49, 1993.

(12) Kabanov, A. V.; Vinogradov, S. V. *Angewandte Chemie-International Edition* 2009, 48, 5418.

(13) Wieland, T.; Bokelmann, E.; Bauer, L.; Lang, H. U.; Lau, H. *Liebigs Ann Chem* 1953, 583, 129.

(14) Dawson, P. E.; Kent, S. B. H. *Annual Review of Biochemistry* 2000, 69, 923.

(15) Dirksen, A.; Meijer, E. W.; Adriaens, W.; Hackeng, T. M. *Chem Commun* 2006, 1667.

(16) Ryadnov, M. G.; Woolfson, D. N. *Journal of the American Chemical Society* 2007, 129, 14074.

(17) Jung, J. P.; Jones, J. L.; Cronier, S. A.; Collier, J. H. *Biomaterials* 2008, 29, 2143.

(18) Hu, B. H.; Su, J.; Messersmith, P. B. *Biomacromolecules* 2009, 10, 2194.

(19) Su, J.; Hu, B. H.; Lowe, W. L.; Kaufman, D. B.; Messersmith, P. B. *Biomaterials* 2010, 31, 308.

We claim:
1. A macromonomer comprising the chemical structure:

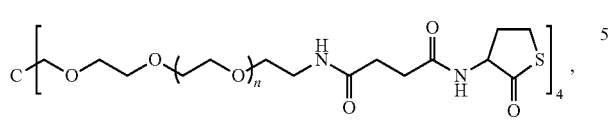

wherein each n has a value in the range of from 0 to 200.

2. A hydrogel obtained by cross-linking the macromonmer of claim 1 and a macromonomer comprising the chemical structure:

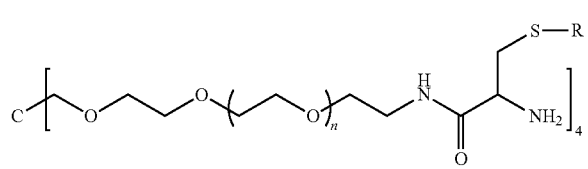

wherein each n has a value in the range of from 0 to 200, and wherein each R is independently selected from the group consisting of H and 4. The hydrogel of claim 2, wherein at least one R is

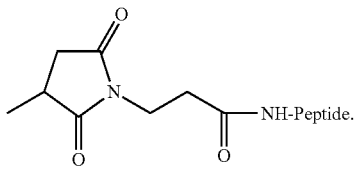

5. The hydrogel of claim 4, wherein the Peptide is from 5 to 20 amino acid residues in length.

6. The hydrogel of claim 5, wherein the Peptide is from 6 to 12 amino acid residues in length.

7. The hydrogel of claim 6, wherein the Peptide is selected from the group consisting of the amide-terminated amino acid sequences GRGDSPG-NH$_2$ (SEQ ID NO:1) and FEW-TPGWYQPY-NH$_2$ (SEQ ID NO:2).

8. The hydrogel of claim 7 wherein the Peptide is the amide-terminated amino acid sequence GRGDSPG-NH$_2$ (SEQ ID NO:1).

9. The hydrogel of claim 3, wherein the hydrogel comprises the chemical structure:

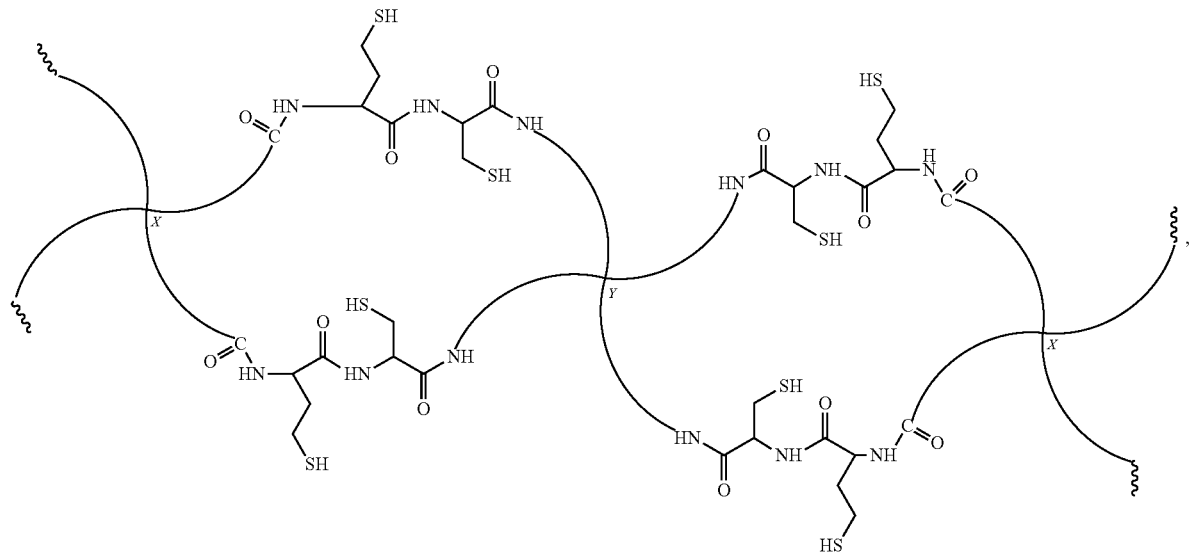

wherein the chemical moiety represented by

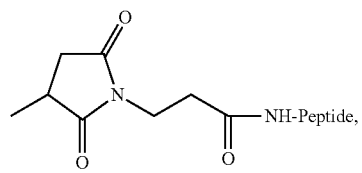

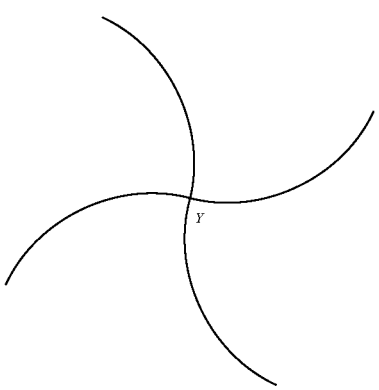

and wherein the hydrogel is cross-linked between the N-terminal cysteamine of the macromonomer of claim 2 and the cyclic thioester of the macromonomer of claim 1.

3. The hydrogel of claim 2, wherein R is H.

has the chemical structure:
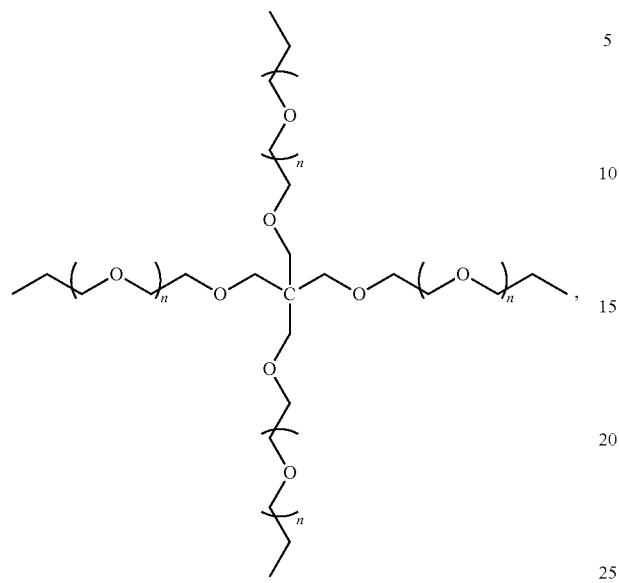
and wherein the chemical moiety represented by
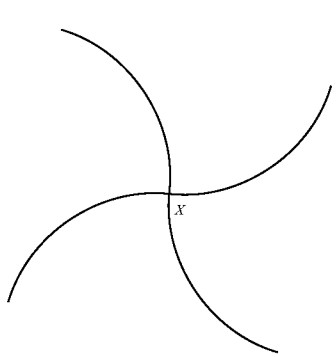
has the chemical structure:
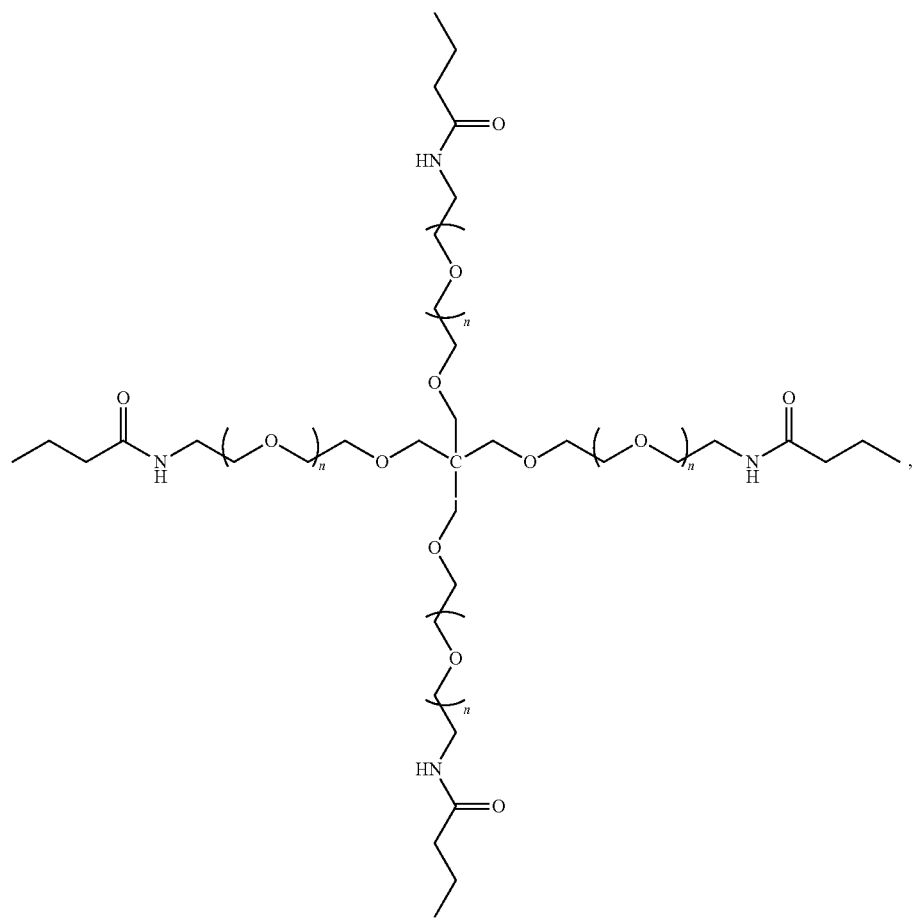
and wherein each n has a value in the range of from 1 to 201.

10. The hydrogel of claim 4, wherein the hydrogel comprises the chemical structure:
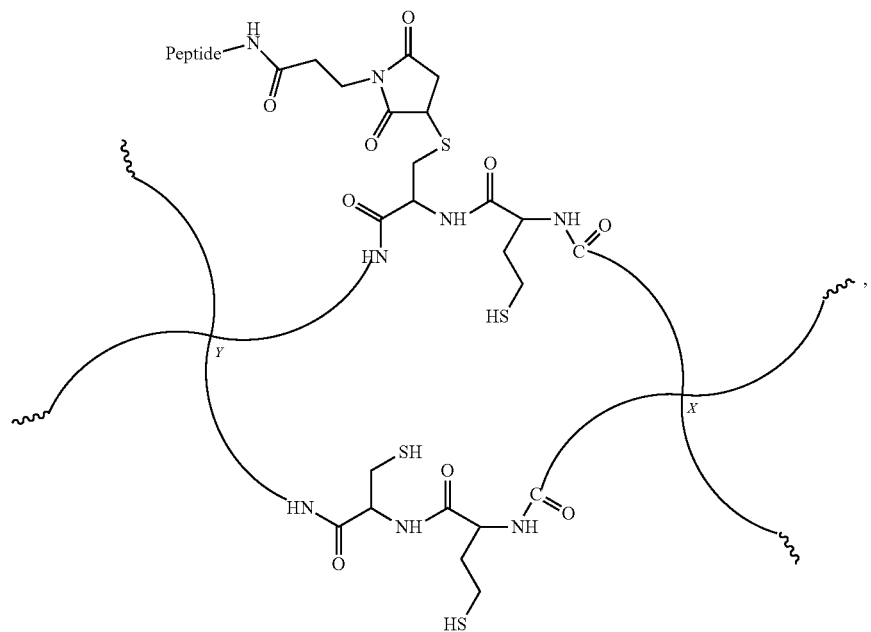
wherein the chemical moiety represented by has the chemical structure:
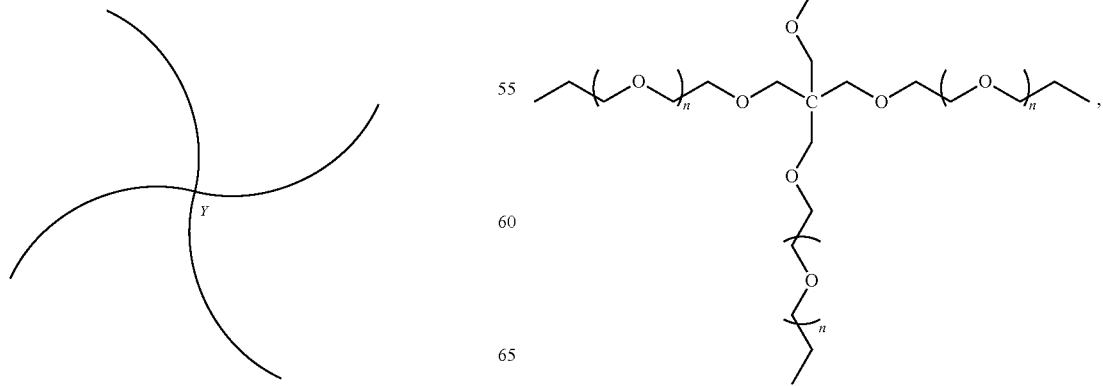

and wherein the chemical moiety represented by

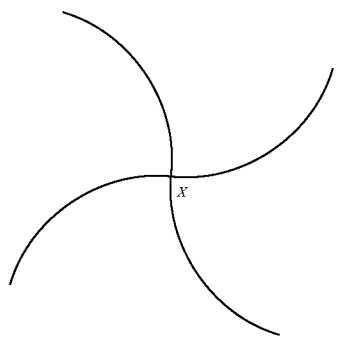

has the chemical structure:

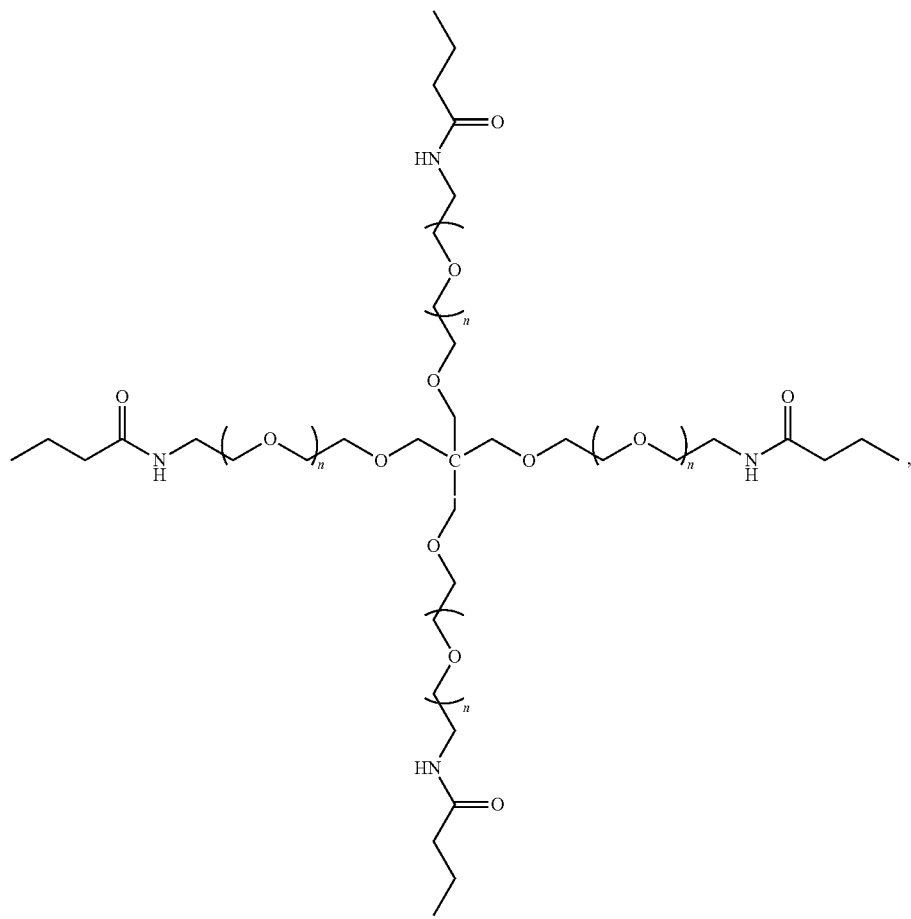

and wherein each n has a value in the range of from 1 to 201.

11. The hydrogel of claim 10, wherein the Peptide is selected from the group consisting of the amide-terminated amino acid sequence GRGDSPG-NH$_2$ (SEQ ID NO:1) and FEWTPGWYQPY-NH$_2$ (SEQ ID NO:2).

12. The hydrogel of claim 11, wherein the Peptide is the mide-terminated amino acid sequence GRGDSPG-NH$_2$ (SEQ ID NO:1).

13. A method of synthesizing a hydrogel comprising covalently cross-linking an effective amount of a first macromonomer comprising a cyclic thioester group with an effective amount of a second macromonomer comprising a terminal cysteine group, wherein the first macromonomer is a macromonomer comprising the chemical structure:

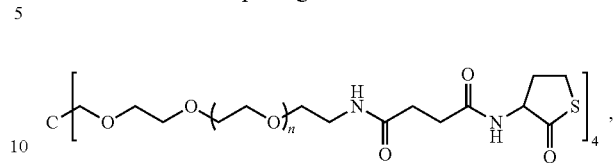

wherein each n has a value in the range of from 0 to 200; and the second macromonomer is a macromonomer comprising the chemical structure:

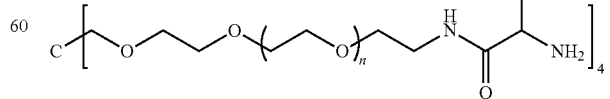

wherein each n has a value in the range of from 0 to 200 and wherein each R is independently selected from the group consisting of H and

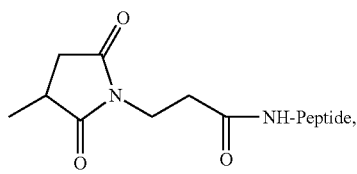

wherein a hydrogel is formed.

14. The method of claim 13 wherein the macromonmers are covalently cross-linked using native chemical ligation.

15. The method of claim 13, wherein R is H.+

16. The method of claim 13, wherein at least one R is

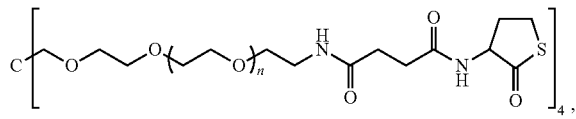

and the Peptide comprises the amine-terminated amino acid sequence GRGDSPG-NH$_2$ (SEQ ID NO:1).

17. A method of synthesizing a macromonomer comprising the chemical structure:

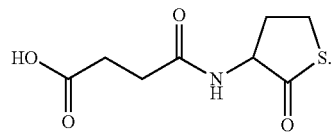

wherein each n has a value in the range of from 0 to 200, the method comprising:

(a) preparing a cyclic thioester, and (b) coupling the cyclic thioester with an amine-terminated 4-armed poly(ethylene glycol);

wherein the macromonomer is formed.

18. The method of claim 17, wherein the cyclic thioester is

19. A method of encapsulating a biological sample with biomaterials comprising:

a) preparing a biocompatible hydrogel according to the method of claim 12;

b) reacting the biocompatible hydrogel with a biomaterial to form a modified biocompatible hydrogel; and c) contacting the biological sample with the modified biocompatible hydrogel, wherein the modified biocompatible hydrogel surrounds and encapsulates the sample.

20. The method of claim 19, wherein the biomaterial is an anti-inflammatory peptide.

21. The method of claim 20 wherein the anti-inflammatory peptide is an inhibitor of cell surface IL-1 receptor.

22. The method of claim 21, wherein the IL-1 receptor has the sequence FEWTPGWYQPY-NH$_2$ (SEQ ID NO:2).

* * * * *

UNITED STATES PATENT AND TRADEMARK OFFICE
CERTIFICATE OF CORRECTION

PATENT NO.        : 9,012,594 B2                                    Page 1 of 1
APPLICATION NO.   : 13/090416
DATED             : April 21, 2015
INVENTOR(S)       : Phillip B. Messersmith, Bi-Huang Hu and Jing Su It is certified that error appears in the above-identified patent and that said Letters Patent is hereby corrected as shown below:

In the Specification
Column 3, line 37, "1.2" should be --12--
Column 12, line 14, "a-amine" should be --α-amine--

In the Claims
Column 33, line 64, "mide-terminated" should be --amide-terminated--
Column 35, line 11, "macromonmers" should be --macromonomers--

Signed and Sealed this
Fifth Day of January, 2016

Michelle K. Lee
*Director of the United States Patent and Trademark Office*